United States Patent [19]

Katz

[11] Patent Number: 5,643,331
[45] Date of Patent: Jul. 1, 1997

[54] METHOD AND DEVICE FOR PREVENTION OF DEEP VEIN THROMBOSIS

[76] Inventor: Amiram Katz, 15 Beaver Brook Rd., Weston, Conn. 06883

[21] Appl. No.: 561,372

[22] Filed: Nov. 21, 1995

[51] Int. Cl.[6] .............................. A61N 1/03; A61N 1/04
[52] U.S. Cl. .............................. 607/48; 607/46; 607/115; 128/639
[58] Field of Search ......................... 128/639; 607/46–49, 607/63, 72, 145, 148–151

[56] References Cited

U.S. PATENT DOCUMENTS

| | | | |
|---|---|---|---|
| 4,157,087 | 6/1979 | Miller et al. | 607/47 |
| 4,702,732 | 10/1987 | Powers | 607/152 |
| 4,759,368 | 7/1988 | Spanton et al. | 607/46 |
| 5,358,513 | 10/1994 | Powell et al. | 607/46 |

FOREIGN PATENT DOCUMENTS

| | | | |
|---|---|---|---|
| 3916994 | 11/1990 | Germany | 607/149 |
| 703101 | 12/1979 | U.S.S.R. | 607/46 |

OTHER PUBLICATIONS

Hirsch, MD, et al; Deep Vein Thrombosis in Medical ICU Patients; JAMA, Jul. 26, 1995–vol 274, No. 4, pp. 335 to 337.

Pambianco, MS, MPH et al; Deep Vein Thrombosis; Prevention in Stroke Patients During Rehabilitation,; Arch Phys Med Rehabil. vol. 76, Apr. 1995; pp. 324 to 330.

Klecker und W. Theiss; Die transkutane elektrische Muskelstimulation–eine "neue" Moglichkeit zur Thromboseprophylaxe?; VASA, Band 23, 1994, Heft 1; pp. 23 to 29.

Anderson, Jr., PhD., et al; A Population–Based Perspective of the Hospital Incidence and Case–Fatality Rates of Deep Vein Thrombosis Thromsis and Pulmonary Embolism; Arch Intern Med–vol. 151, May 1991; pp. 933 to 938.

*Primary Examiner*—William E. Kamm
*Assistant Examiner*—George R. Evanisko
*Attorney, Agent, or Firm*—Fattibene and Fattibene; Paul A. Fattibene; Arthur T. Fattibene

[57] ABSTRACT

An electrical stimulator and method of prevention of deep vein thrombosis, ankle edema, and venostasis. An electronic circuit that includes a power source and a micro controller for processing the signals generated by a duration control circuit, a frequency control circuit, and an intensity control circuit so as to generate a square wave pattern or wave form having a controllable duration ranging between 0.1 to 0.3 milliseconds, a controllable frequency ranging between 0.001 to 0.1 cycles per seconds, and a controllable intensity ranging between 1 to 20 milliamperes. In application, an electrode portion having an exposed juxtapositioned anode and cathode is secured to the patient externally at or near the tibial nerve at the popliteal fossa, on both legs. The specific wave pattern generated stimulates the nerve causing a muscle contraction, whether passively or actively, of the calves which prevents deep vein thrombosis, ankle edema, and venostasis.

8 Claims, 3 Drawing Sheets

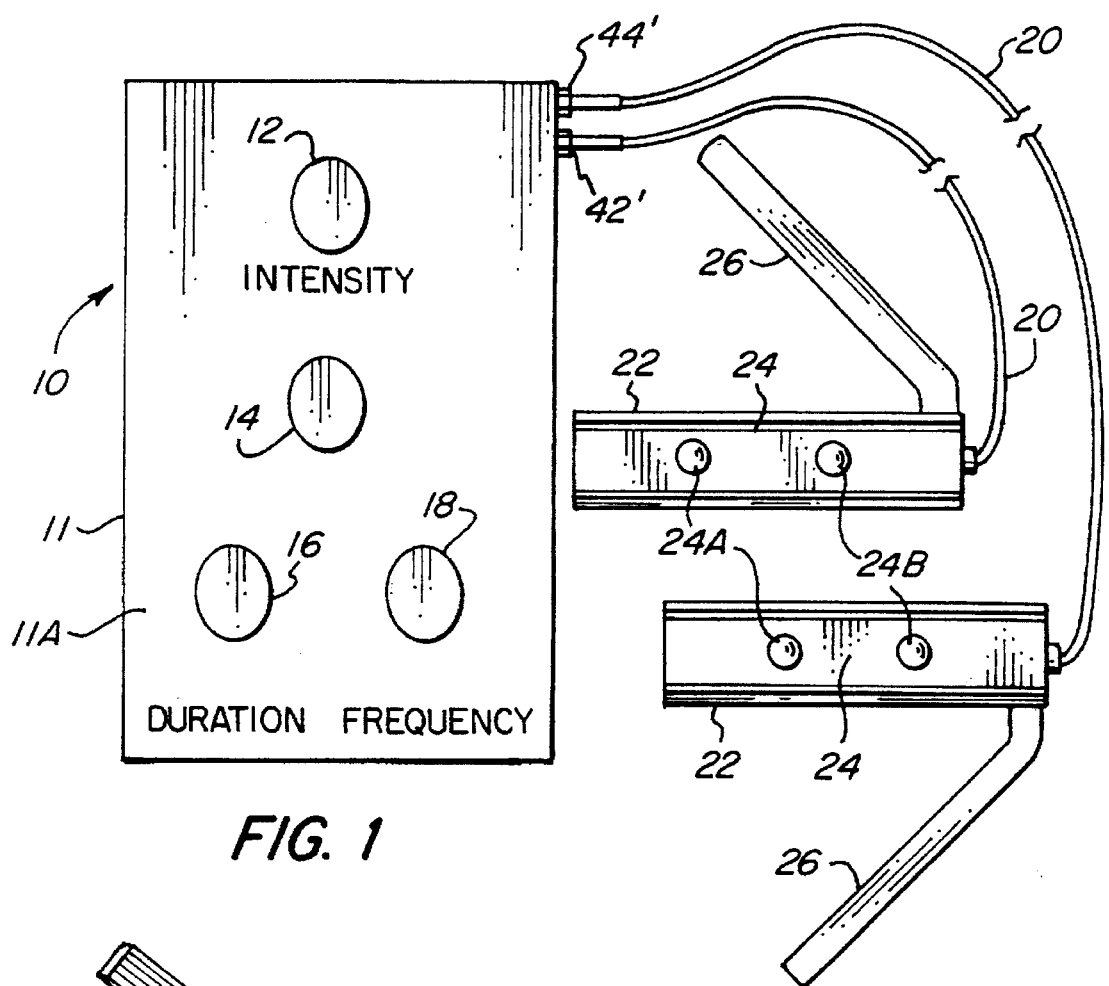
FIG. 1
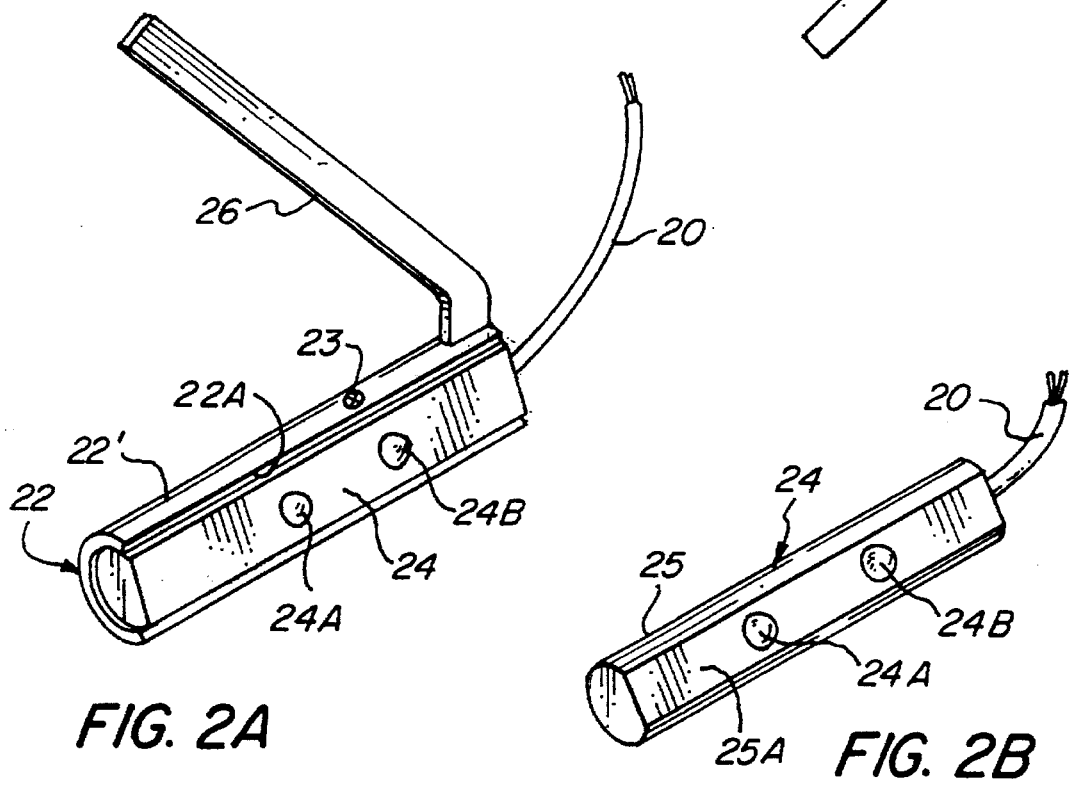
FIG. 2A
FIG. 2B

METHOD AND DEVICE FOR PREVENTION OF DEEP VEIN THROMBOSIS

FIELD OF THE INVENTION

This invention relates to an electronic stimulator, and more specifically to an electronic nerve stimulator and method useful for preventing deep vein thrombosis, ankle edema, and venostasis.

BACKGROUND OF THE INVENTION

Deep vein thrombosis (DVT) is a common medical condition that may be potentially fatal by becoming a source or lead to pulmonary emboli (PE). DVT is especially common in patients who are immobilized for relatively long periods of time due to a medical or surgical illness, or patients with multiple trauma, or patients with malignant diseases, or patients who are paraplegic and quadriplegic, pregnant, and/or having other medical conditions. It can also develop in otherwise healthy individuals, after prolonged sitting and immobilization. Current treatments may comprise anticoagulation, which may carry significant inherent risks, surgical approaches (for prevention of PE after DVT has developed) of various filter installations, which are not completely effective, and the attempted prevention of DVT by mechanical devices such as graduated leg stockings, external pneumatic calf compression, and pharmacological agents such as low does of Heparin or Coumadin.

The main cause of DVT is venous stasis, i.e., the lack of effective venous blood flow from the calves due to extended periods of immobilization. A very effective means for preventing DVT is muscle contraction of the calves which pumps centrally venous blood, thus preventing stasis in the proximal veins, e.g., pelvis as well. If a patient can continuously move his or her legs or exercise, e.g., "a stepping on brakes" movement against a leg board, many cases of DVT can be prevented. However, most of the patients that develop DVT are not in a condition to so exercise voluntarily.

Such lack of efficient or effective venous flow from the legs can result in other problems which, while they may not be life threatening, are associated with significant discomfort and are aesthetically unappealing, e.g., idiopathic ankle edema and edema associated with venostasis and varicose veins. Effective muscle pumping can significantly reduce the morbidity associated with these conditions also.

PRIOR ART

There exists a number of transcutaneous electrical nerve stimulators, commonly known as TENS units. Such TENS units are utilized primarily to reduce or minimize the sensation of pain such as back pain, lumbago, cervical pain, temporomandibular joint pain (TMJ), tendinitis, tennis elbow and the like. In theory, the known TENS units are designed to overload the sensory nerve endings so as to block or prevent the pain messages to be sent to the brain. The principal manufacturers of such TENS units include Medronics, 3M and others.

Other muscle and neurological stimulators (MANS) are known. MD Products of Ocala, Fla., produces one such device. These devices, like the TENS units, generate a wave form to relieve acute or chronic pain, e.g., such that may be associated with TMJ. However, the recent studies (Pambianco, Orchard and Landau; and Klecker and Theiss) that mention the use of electric muscle stimulators as a potential prophylactic method indicate that the muscle was stimulated to an observable minor motion, and that such stimulation resulted in pain and local blistering, e.g., by stimulation frequency of 25–50 Hertz which was not tolerated well by the patients. As a result, the studies were early terminated in these patients, without the ability to compare the effectiveness of the treatment to other modalities. In these studies, the commercially available muscle stimulators and TENS were used.

SUMMARY OF THE INVENTION

An object of this invention is to provide a relatively small electronic stimulator for simulating a voluntary effective muscle contraction of the calves by electrically activating the muscle via a major motor nerve stimulation. Alternatively, the device will supply small currents to stimulate sensory nerves, in order to initiate voluntary movements in patients or individuals who are able to do so.

Another object is to provide an electronic device that will generate a square wave with a controllable duration of 0.1 to 0.3 milliseconds, a frequency of 0.001 to 0.1 cycles per second and an intensity of 1 to 20 milliamperes.

Another object is to provide an electronic nerve-muscle stimulator capable of producing a frequency which is $1/1,000$ of the frequency generated by the known TENS units or muscle simulators so as to minimize any burns or blisters which have been reported with the known conventional TENS units.

The foregoing objects and other features and advantages are attained by an electronic device having a circuitry that will generate a square wave with a controllable duration of 0.1 to 0.3 milliseconds, a frequency in the range of 0.001 to 0.1 cycles per second, and an intensity ranging between 1 to 20 milliamperes. The arrangement is such that the device will simulate a voluntary effective muscle contraction of the calves by electrically activating the muscle via a major motor nerve stimulation, or alternatively, the device will supply small currents to stimulate sensory nerves, in order to initiate or effect a voluntary movements in patients or individuals who are able to do so. Included are stimulating electrodes that are applied externally to the tibial nerve at the popliteal fossa. The electrodes, comprising an anode and a cathode and specially constructed for nerve stimulation, have a generally cylindrical or disk shape with an approximate 0.25 inch diameter having a flat surface area. An electrode portion holds the anode and cathode proximately located on a flat surface, and separated from each other by approximately 1.5 inches or 3.1 centimeters, center to center. The electrode portions is rotatably disposed within a holder having an attachment arm connected thereto for supporting the electrodes in the right anatomic location without compressing the limb and impeding venous flow.

IN THE DRAWINGS

FIG. 1 is a general overall view of an electronic stimulator embodying the invention.

FIG. 2A is a detail perspective view illustrating the electrode portion and associated electrode holder.

FIG. 2B is a detail perspective view of the electrode portion of this invention.

DETAILED SPECIFICATION

Figure 3:
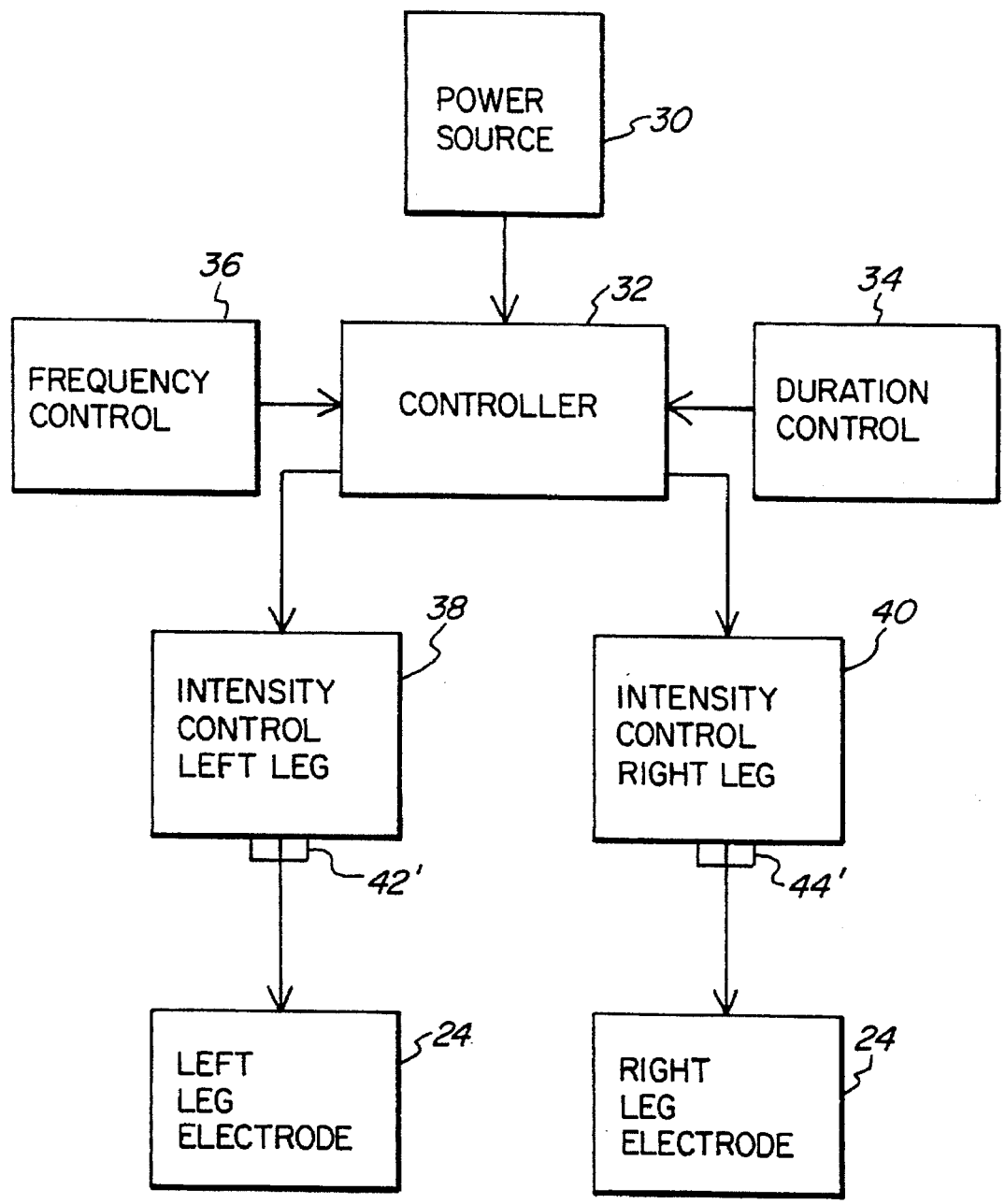
FIG. 3 is a schematic block diagram of the electronic stimulator embodying the invention.

Referring to FIG. 1, there is illustrated an embodiment of the invention. As shown, the electronic nerve stimulator 10 embodying the invention comprises a housing 11 containing the electrical components shown in FIGS. 3 and 5. Connected to suitable jack outlets 42', 44', are detachably connected leads or conductors 20 to which the respective electrode portion 24 are connected. In the illustrated embodiment, the respective electrode portion 24 comprise an elongated cylindrical member 25 having a flattened face portion or surface 25A on which an anode 24A and cathode 24B are mounted. It will be understood that the leads 20 comprise a two-wire conductor in which the respective wires are connected to its corresponding anode 24A and cathode 24B.

In order to accurately position the electrode portion 24 to that portion of the body which is to be stimulated, e.g., the tibial nerve at the popliteal fossa, an electrode holder 22 is provided. As shown in FIGS. 2A and 2B, the electrode holder 22 comprises a generally C shaped body 22' for slidably receiving the electrode portion 24 so that the flattened surface 25A of the electrode portion 24 containing the anode 24A and cathode 24B are exposed through the cut out portion 22A of the holder body 22'. Connected to the holder body is a bendable attachment arm 26 which can be suitably bent to any desired angle to position the anode 24A and cathode 24B in the optimum position for stimulating the nerve. The holder 22 is maintained in position opposite the nerve to be stimulated by taping the attachment arm 26 to the patient. In the arrangement described, it will be noted that the electrode portion 24 can be rotated within the holder body 22' to a limited extent so as to permit adjustment of the anode and cathode to the body of the patient within a predetermined range. Additionally, the electrode portion 24 can be positioned longitudinally within the holder 22. A set screw 23 is provided to maintain the electrode portion 24 in its adjusted position within the holder 22.

As indicated in FIG. 1, the controls for regulating the intensity, duration and frequency comprise control knobs located on the face 11A of the housing 11. As shown, a left intensity control knob 12 and a right intensity control knob 14 are provided on the housing to control the amount of current or amperes. In addition, a duration control knob 16 and a frequency control knob 18 are also mounted in the face of the housing. The circuitry controlled by the respective control knobs 12, 14, 16, and 18 is illustrated in FIGS. 3 and 5.

Referring to FIG. 3, there is shown in block diagram form the circuit which includes a suitable power source 30, e.g., a rechargeable 9 V battery operatively connected to a micro controller 32 which may comprise a CPU controller. Coupled to the micro controller 32 is a duration control circuit 34 and frequency control circuit 36. Also coupled to the micro controller 32 is an intensity control circuit 38 for the left leg and an intensity control circuit 40 for the right leg. The respective intensity control circuits 38 and 40 include an outlet or jack 42', 44' respectively, to which the leads 20 of the respective electrodes 24 are detachably connected, as illustrated in FIG. 1.

Figure 5:
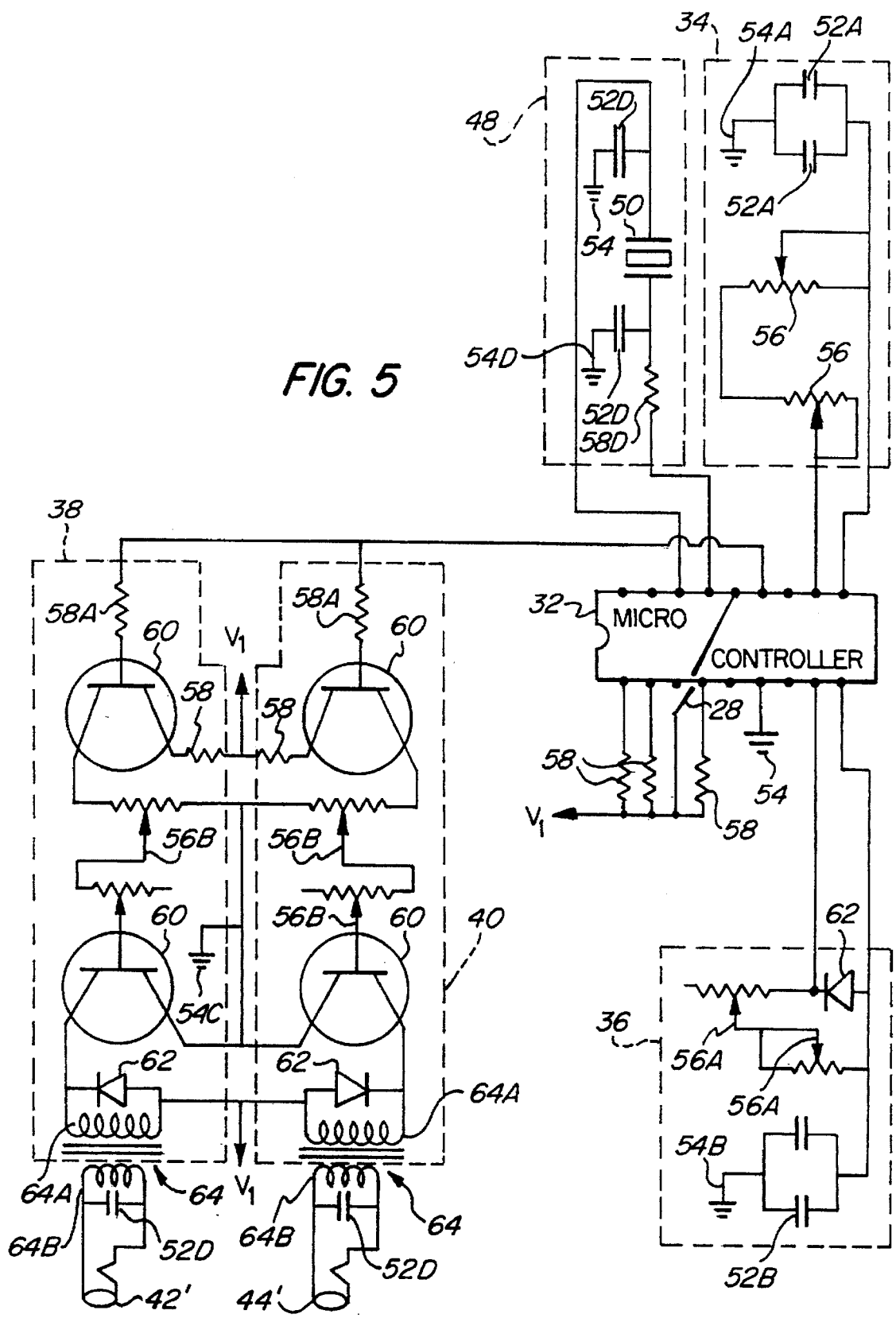
FIG. 5 illustrates the circuitry of the invention.

FIG. 5 illustrates the circuit diagram for practicing the present invention. The circuit includes the controller or CPU 32 which is powered by an input voltage $V_1$ generated by a power source such as a rechargeable battery, e.g., nine (9) volt battery or a suitable AC adaptor. The input voltage $V_1$ is coupled to the controller 32 through resistors 58 and a switch 28. The controller 32 is also connected to ground 54. The duration control circuit or portion 34 of the circuit comprises a pair of variable resistors 56 and a pair of capacitors 52A. One electrode of the respective capacitors 52A is connected to ground 54A.

The frequency control portion 36 comprises a pair of variable resistors 56A, a diode 62 and a pair of capacitors 52B. One electrode of the respective capacitors 52B are connected to ground 54B. Each of the left and right leg intensity control circuits or portions 38 and 40 include resistors 58A, transistors 60, variable resistors 56B, diodes 62, and the primary 64A of transformers 64. Each of the left and right leg intensity controls 38 and 40 are also coupled or connected to ground 54C and the input voltage $V_1$.

The secondaries 64B of the respective transformers 64 are coupled to the left and right leg output jacks 42' and 44'. Capacitors 52D are connected in parallel with the secondary 64B of the transformers 64. Additionally, coupled to the controller 32 is an oscillator 48. The oscillator 48 includes a crystal 50, a resistor 58D, and capacitors 52D. One electrode of each of the capacitors 52D is connected to ground 54D.

Figure 4:
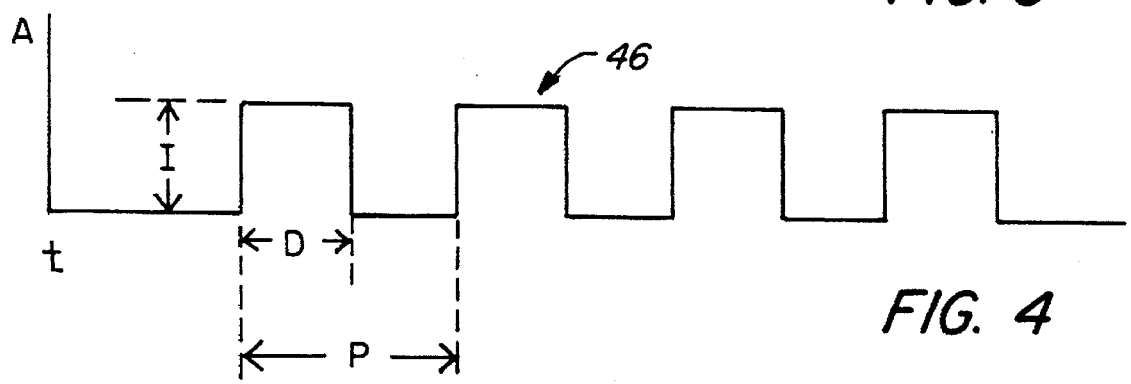
FIG. 4 is an illustrated wave form generated by the electronic device of this invention.

FIG. 4 illustrates the square wave pattern 46 generated by the described circuit. The intensity or amplitude of the wave is illustrated as I. The length of time or duration of the duty or non-zero portion of the wave is illustrated as D. The period of the wave is illustrated as P. The frequency is proportional to the reciprocal of the period.

Referring to FIGS. 3 and 4, the operation of the present invention should be readily appreciated. The frequency control knob 18 controlling the output of the frequency control portion 36 of the circuit coupled to the micro controller 32 and subsequently to the left and right leg electrodes 24 regulates the frequency of the wave 46 shown in FIG. 4. According to the present invention, the frequency may range from 0.001 to 0.1 cycle per second. The duration of the wave 46 is regulated by the duration control knob 16, which controls the output of the duration control portion 34 of the circuit. The duration of the wave 46 may range from 0.1 to 0.3 milliseconds. The left leg intensity is regulated by the control knob 12 which controls the output of the left leg intensity portion 38 of the circuit and the right intensity control knob 14 regulates the output of the intensity control portion 40 of the circuit. According to this invention, the respective intensities to the right and left leg may range between 1 to 20 milliamperes. As a result, the effect of contraction of both the anterior and posterior tibial muscles is achieved by adjusting the duration and intensity. Clinical needs will establish the optimum stimulation frequency. Alternatively, the device will supply small currents to stimulate sensory nerves in order to initiate voluntary movements or muscle contractions, in patients or individuals who are able to do so.

The foregoing described device comprises a readily effective and compact device for alleviating a serious problem which can be operated by the patient himself or with the help of a doctor or physical therapist.

The device is readily portable and compact wherein all of the circuit can be housed in a housing 11 having an overall dimension of approximately 4"×2.5"×1", and utilizing a 9-volt battery as its power source, which may be a rechargeable battery. Alternatively, the stimulator described may be powered by an AC adaptor connected to ordinary 110 AC power.

In operation, the electrode portions 24 are applied to the area to be treated by taping the attachment arm 26 of the holder to the patient and positioning the cut out portion 22A of the holder 22 so that, with the electrode portion 24 in place, the anode 24A and cathode 24B are in contact with the area contiguous to the nerve to be stimulated, e.g., the tibial nerve. The intensity control knobs 12, 14, the duration knob 16, and frequency knob 18 are then adjusted to their requisite intensity and duration settings, with the frequency setting being established by the needs of a given patient. When energized, a square wave pattern is generated with a controllable duration ranging between 0.1 to 0.3 milliseconds, a frequency ranging between 0.001 and 0.1 cycles per second, and an intensity for the left and right legs ranging between 1 to 20 milliamperes. Effective contraction of both anterior and posterior calf tibial muscles is achieved by adjusting the duration and intensity control knobs 12, 14 and 16. As a result, an effective muscle pumping is achieved to reduce the morbidity associated with DVT, ankle edema or venostasis. Alternatively, the device will supply small currents to stimulate sensory nerves, in order to initiate voluntary movements in patients or individuals who are able to do so.

While the invention has been described with respect to a particular embodiment of the invention, variations and modifications may be made without departing from the spirit or scope of the invention.

What is claimed is:

1. An electronic stimulator for the prevention of deep vein thrombosis, ankle edema and venostasis comprising:
   a circuit generating a square wave pattern and having
      a circuit portion for varying the frequency of said wave pattern within a predetermined range of 0.001 to 0.1 cycles per second;
      a second circuit portion to vary the duration of said wave pattern within a predetermined range of 0.1 to 0.3 milliseconds;
      a third circuit portion to vary the intensity of said wave pattern within a predetermined range of 1 to 20 milliamperes, said third circuit portion having an output;
   a pair of electrode portions operatively connected to the output of said third circuit portion;
   each of said pair of electrode portions including a juxtapositioned anode and cathode; and
   a holder for supporting each of said pair of electrode portions, wherein said holder comprises
      a cylindrically shaped body having a longitudinally extending cut-out portion to define an opening having a width which is less than the diameter of said body,
      and each of said pair of electrode portions having a cylindrical shape complementing said cylindrical body,
      said electrode portion having a flattened face surface arranged to be disposed in alignment with said opening of said cylindrically shaped body,
      said anode and cathode being juxtapositioned on said flattened face surface of said electrode portion,
      and an attachment arm connected to said holder for securing said holder and associated electrode portion to the body of a patient.

2. An electronic stimulator as defined in claim 1 wherein said electrode portion is sized to be rotatably disposed with said holder within predetermined limits,
   and means for securing said electrode in an adjusted position within said holder.

3. A method of preventing deep vein thrombosis, ankle edema and venostasis comprising the steps of
   generating a square wave signal having a duration of 0.1 to 0.3 milliseconds, a frequency of 0.001 to 0.1 cycles per second, and an intensity of 1 to 20 milliamperes, and
   applying said signal to a major motor nerve to electrically activate an associated muscle.

4. A method of preventing deep vein thrombosis, ankle edema and venostasis comprising the steps of
   generating a square wave signal having a duration of 0.1 to 0.3 milliseconds, a frequency of 0.001 to 0.1 cycles per second, and
   applying said signal to a major motor nerve to providing a sensory stimulation to effect a voluntary movement.

5. The method as defined in claim 4 and including the step of applying said signal to the tibial nerve at the popliteal fossa in both legs of a given patient.

6. An electrical device for preventing deep vein thrombosis, ankle edema, or venostasis comprising:
   a controller, said controller generating a substantially square wave signal;
   a frequency control, said frequency control coupled to said controller, said frequency control providing a frequency in a range between 0.001 and 0.1 cycles per second;
   a duration control, said duration control coupled to said controller, said duration control providing a duration in a range between 0.1 and 0.3 milliseconds;
   a right leg intensity control, said right leg intensity control coupled to said controller, said right leg intensity controls provide an intensity in a range between 1 and 20 milliamperes;
   a left leg intensity control, said left leg intensity control coupled to said controller, said left leg intensity controls provide an intensity in a range between 1 and 20 milliamperes;
   a right leg electrode portion coupled to said right leg intensity control;
   a left leg electrode portion coupled to said left leg intensity control;
   a first C shaped body, said first C shaped body adjustably holding said right leg electrode portion;
   a second C shaped body, said second C shaped body adjustably holding said left leg electrode portion;
   a first set screw associated with said first C shaped body and contacting said right leg electrode portion holding it in place;
   a second set screw associated with said second C shaped body and contacting said left leg electrode portion holding it in place;
   a first attachment arm connected to said first C shaped body; and
   a second attachment arm connected to said second C shaped body,
   whereby said right and left leg electrodes may be precisely adjusted and held in place on the patient's legs, and positioned on a patient's legs for providing an electrical stimulus to a nerve causing muscular contraction increasing venous flow in the patient's legs.

7. A stimulator for use in the prevention of deep vein thrombosis comprising:
   signal means for generating an electrical signal, said signal means having an output;
   a frequency control coupled to said signal means;
   a duration control coupled to said signal means;
   an intensity control coupled to said signal means;
   a cylindrically shaped electrode portion, said electrode portion coupled to the output;
   a cylindrically shaped body, said cylindrically shaped body having a longitudinally extending cut-out portion and placed over said cylindrically shaped electrode portion exposing a portion of said cylindrically shaped electrode portion;

securing means, associated with said cylindrically shaped body, for securing said cylindrically shaped electrode within said cylindrically shaped body; and an arm attached to said cylindrically shaped body, whereby the position of said cylindrically shaped electrode is accurately adjusted and maintained.

8. A method of preventing deep vein thrombosis, ankle edema and venostasis comprising the step of:

applying an electrical signal having a frequency of 0.001 to 0.1 cycles per second, a duration of 0.1 to 0.3 milliseconds, and an intensity of 1 to 20 milliamperes to a leg of a patient so as to cause contraction of both the anterior and posterior tibial muscles, whereby deep vein thrombosis, ankle edema, and venostasis is prevented in an immobilized patient while minimizing the risk of burns or blisters.

* * * * *